(12) United States Patent
Hineno

(10) Patent No.: US 8,475,392 B2
(45) Date of Patent: Jul. 2, 2013

(54) NEEDLE FOR LIVING BODY, TISSUE-SAMPLING DEVICE AND PROCESS FOR SAMPLING TISSUE

(75) Inventor: Hitoshi Hineno, Chigasaki (JP)

(73) Assignee: Kabushiki Kaisha Pilot Corporation, Tokyo-To (JP)

( * ) Notice: Subject to any disclaimer, the term of this patent is extended or adjusted under 35 U.S.C. 154(b) by 486 days.

(21) Appl. No.: 12/815,533

(22) Filed: Jun. 15, 2010

(65) Prior Publication Data

US 2010/0324447 A1    Dec. 23, 2010

(30) Foreign Application Priority Data

Jun. 17, 2009    (JP) .................................. 2009-144054

(51) Int. Cl.
*A61B 10/00*    (2006.01)
*A61B 17/32*    (2006.01)
*A61B 17/14*    (2006.01)

(52) U.S. Cl.
USPC ........... 600/564; 600/562; 600/563; 600/565; 600/566; 600/567; 606/167; 606/170; 606/184

(58) Field of Classification Search
USPC ... 600/562–567, 570, 571; 604/272; 606/160, 606/167, 170, 184, 185
See application file for complete search history.

(56) References Cited

U.S. PATENT DOCUMENTS

| 5,133,360 | A  | * | 7/1992 | Spears .......................... | 600/567 |
| 5,645,537 | A  | * | 7/1997 | Powles et al. ................. | 604/240 |
| 6,849,051 | B2 | * | 2/2005 | Sramek et al. ................ | 600/565 |
| 2009/0099535 | A1 | * | 4/2009 | Wang et al. ................... | 604/272 |

FOREIGN PATENT DOCUMENTS

| JP | 2002-085413 | 3/2002 |
| JP | 2008-307072 | 12/2008 |

OTHER PUBLICATIONS

English abstract of publication: JP 2002-085413.
English abstract of publication: JP 2008-307072.

* cited by examiner

*Primary Examiner* — Sean P Dougherty
*Assistant Examiner* — Devin Henson
(74) *Attorney, Agent, or Firm* — Quarles & Brady LLP

(57) ABSTRACT

This invention provides a needle for a living body and a process for sampling a tissue with the needle. The needle and the process are used for harvesting a tissue sample from a living body with minimal damage. The needle is made of ceramics, and is provided with a sampling hole for aspirating a sample and with a cooling hole for supplying cooling gas. The holes penetrate through in the longitudinal direction, and have openings on a pricking-end surface of the needle. For the purpose of cutting off the tissue sample, the pricking-end surface is provided with a cutting part positioned between the openings. When the needle is pricked into a body, a tissue is aspirated through the sampling hole while cooling gas is being supplied through the cooling hole. Thus, the tissue is partly frozen or semi-frozen and cut off with the cutting part to harvest by aspiration.

7 Claims, 5 Drawing Sheets

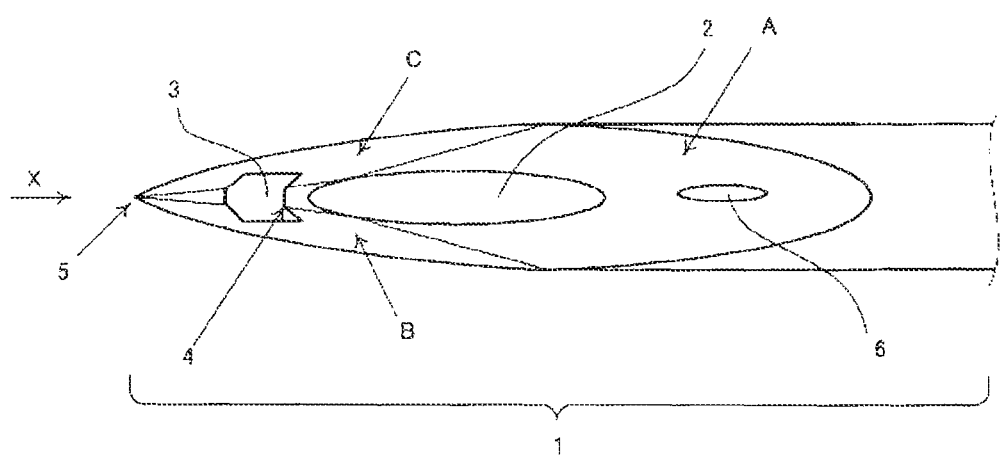
Fig. 7
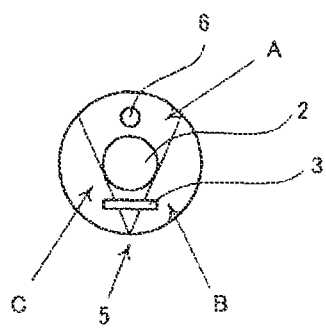
Fig. 8
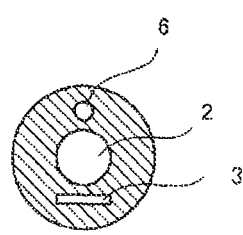 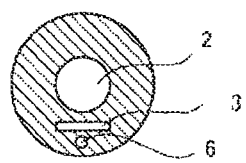 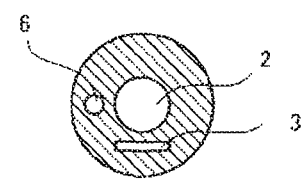
Fig. 9A Fig. 9B Fig. 9C

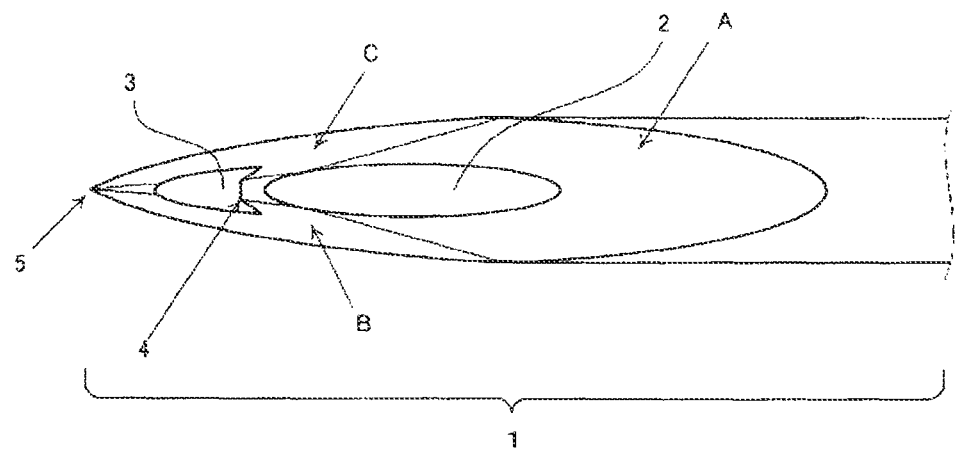
Fig. 10
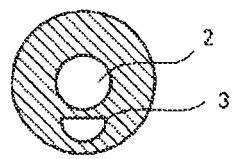
Fig. 11
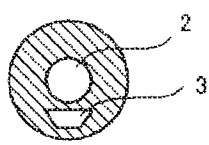　　　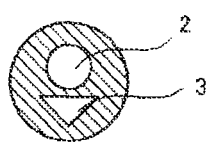
Fig. 12A　　　Fig. 12B

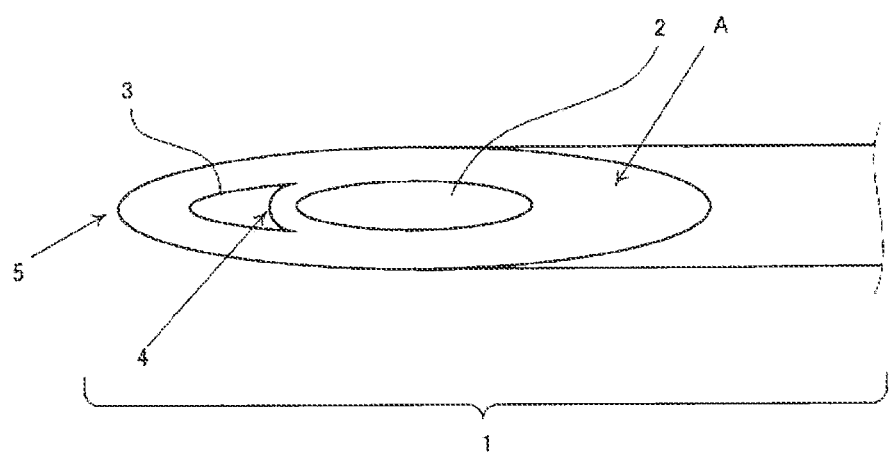
Fig. 13
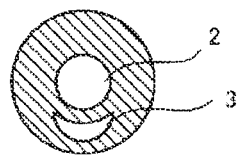 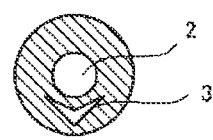
Fig. 14          Fig. 15

NEEDLE FOR LIVING BODY, TISSUE-SAMPLING DEVICE AND PROCESS FOR SAMPLING TISSUE

CROSS-REFERENCE TO RELATED APPLICATION

This application is based upon and claims the benefit of priority from the prior Japanese Patent Application No. 2009-144054, filed on Jun. 17, 2009; the entire contents of which are incorporated herein by reference.

BACKGROUND OF THE INVENTION

1. Field of the Invention

This invention relates to a needle used for sampling a tissue from a living body so as to diagnose or treat a disease. Specifically, the present invention relates to a needle that makes it possible to harvest a tissue sample from a living body favorably enough to reduce damage of the harvested sample to a minimum and effectively enough to obtain precise information.

2. Background Art

Needles for living bodies, such as biopsy needles and therapeutic needles, are often employed for diagnosing or treating diseases of human and animals. The needles for living bodies are pricked into skins or the like of creatures, so as to inject medicines or to pluck out tissues by use of the tips of the pricked needles. In the case where the needles are applied to human bodies and the like, they are required to damage tissues to a minimal degree. Specifically, since biopsy needles are used for sampling tissues from living bodies for the purpose of obtaining precise information of diseases, the tissue samples are harvested from organs or the like in the bodies preferably without being damaged. This is because the precise information of diseases is hard to obtain if the tissues are damaged when sampled.

Meanwhile, biopsy needles and therapeutic needles have been made of metals such as stainless steel because metals are excellent in rustproof characteristics, in elasticity and in tension resistance and also are easily formed into sharp shapes. However, since having electroconductivity and magnetism, metal needles are known to cause injury current when brought into contact with living bodies and, as a result, to damage almost all the cells in contact therewith. Accordingly, tissue samples harvested with metal needles are often so damaged that it is difficult to obtain precise information of diseases therefrom.

For coping with the above problem, it is proposed (Japanese Patent Laid-Open (KOKAI) No. 2002-85413) to adopt a metal hollow capillary needle coated with a super-hard, non-electroconductive and non-magnetic substance. This needle enables to pluck out a tissue from the aimed site without bringing the tissue into contact with the electroconductive and magnetic metal, and therefore the injury current can be avoided to keep the tissue from being damaged. Consequently, the proposed needle makes it possible to obtain precise information of diseases.

However, even if a metal needle for a living body is coated with a non-electroconductive substance like the above proposed needle, the inside wall of the penetrating hole, namely, the surface of the flow path is covered with such a thin coating film as is liable to peel off or to crack to be destroyed as time elapses. Further, when the needle is only slightly distorted, the coating film often comes off. As a result, the sampled tissue may be brought into contact with metal, and hence the effect of the coating is often insufficiently obtained. In addition, since the coated needle itself is still mainly made of metal like the conventional metal needle, it cannot solve problems of disposal after use.

In view of the above, the inventors have proposed a new needle made of only ceramics (Japanese Patent Laid-Open (KOKAI) No. 2008-307072). The proposed needle for a living body can improve the production cost as well as the damage of tissues caused by the injury current.

SUMMARY OF THE INVENTION

However, it is also desired to improve the mechanism of sampling a tissue at the pricked point. In the conventional mechanism, the tissue is aspirated with an aspiration hole at the tip of the needle and hence is mainly torn off. Accordingly, the tissue is sampled inefficiently and may suffer unnecessary stress to be damaged.

The present invention resides in a needle for a living body made of ceramics, which is used for harvesting a tissue sample from a living body, comprising
in the longitudinal direction, a sampling hole penetrating through for sample aspiration and a cooling hole penetrating through for supplying cooling gas; wherein
said sampling hole and said cooling hole have openings on a surface at the pricking end, where a cutting part for cutting off said tissue sample is provided between said openings.

The present invention also resides in a tissue-sampling device comprising: the above needle for a living body, a pressure-reducing equipment connected to said sampling hole penetrating through for sample aspiration, and a cooling-gas supplying equipment connected to said cooling hole penetrating through for supplying cooling gas.

The present invention further resides in a process for sampling a tissue, wherein
the above needle for a living body is pricked into a living body, and a tissue is aspirated through said sampling hole while cooling gas is being supplied through said cooling hole so as to make a portion of the tissue fragile by freezing or semi-freezing, and then the frozen or semi-frozen portion of the tissue is cut off with said cutting part to harvest the tissue by aspiration.

When pricked into a living body to harvest a tissue sample, the needle of the present invention does not cause injury current. Further, the needle according to the present invention is provided with a structure that enables the pricking tip to harvest the tissue sample efficiently. Accordingly, the living body and the tissue sample are damaged little enough to obtain precise and accurate information. If fully made of ceramics, the needle of the present invention is so stable that it can be repeatedly sterilized to use. In addition, before crashed to be scrapped, this needle can be subjected to thermal treatment at a temperature lower than metal needles. This means that secondary infection can be easily prevented, and hence the needle of the present invention after use can be easily disposed of.

BRIEF DESCRIPTION OF THE DRAWINGS

FIG. 7 is a plane view of the needle for a living body according to the present invention in Example 3.

FIG. 8 is a front view of the needle for a living body according to the present invention in Example 3.

FIG. 9 shows cross-sectional views of needles according to some embodiments of the present invention.

FIG. 10 is a plane view of the needle for a living body according to the present invention in Example 4.

FIG. 11 is a cross-sectional view of the needle for a living body according to the present invention in Example 4.

FIG. 12 shows cross-sectional views of needles according to other embodiments of the present invention.

FIG. 13 is a plane view of a needle according to an embodiment of the present invention.

FIG. 14 is a cross-sectional view of a needle according to another embodiment of the present invention.

FIG. 15 is a cross-sectional view of a needle according to still another embodiment of the present invention.

DETAILED DESCRIPTION OF THE INVENTION

The needle of the present invention for a living body enables one to harvest a tissue sample with minimal damage and accordingly to obtain precise information of diseases from the sample. The present invention is further explained by use of the following examples.

Example 1

Figure 1:
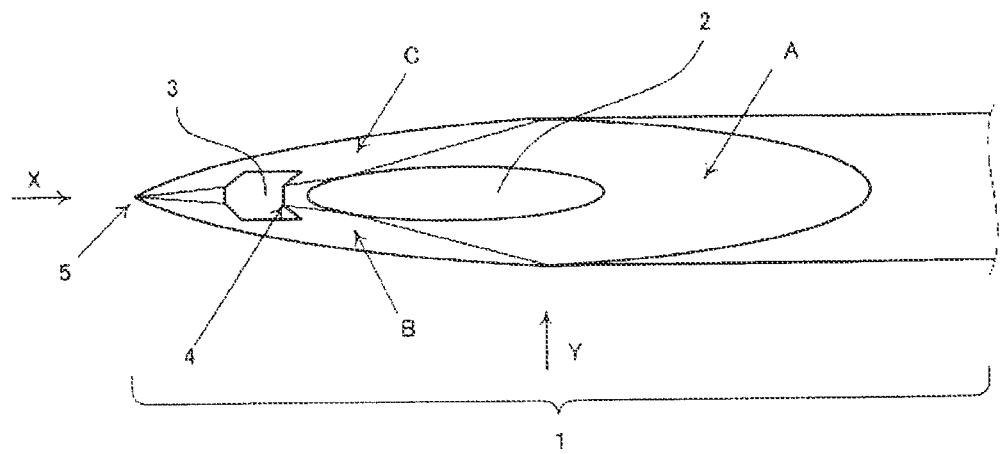
FIG. 1 is a plane view of the needle for a living body according to the present invention in Example 1.
Figure 2:
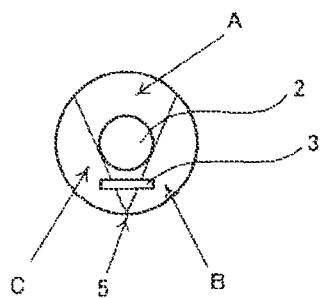
FIG. 2 is a front view of the needle for a living body according to the present invention in Example 1.

FIG. 1 is a plane view showing the pricking end of a needle 1 according to an embodiment of the present invention, and FIG. 2 is a front view thereof seen parallel to the longitudinal direction (in the direction indicated by the arrow X in FIG. 1). Further, FIG. 3 is a side view thereof seen perpendicularly to the longitudinal direction (in the direction indicated by the arrow Y in FIG. 1).

The needle of the present invention is made of ceramics, and is provided with at least two holes penetrating through in the longitudinal direction. One of the holes is a sampling hole 2 for aspirating a sample, and the other is a cooling hole 3 for supplying cooling gas. The surface at the pricking end is a bevel having a sharp pricking tip 5. When the needle is pricked into a body, the pricking tip 5 is first brought into contact with the body. The needle of the present invention is also provided with a cutting part 4 positioned between openings of the holes on the pricking-end surface. This is one of the characteristics of the needle according to the present invention. When the needle is pricked into a body to harvest a tissue by aspiration, the cutting part 4 plays a role of cutting the aspirated tissue off from the body.

Figure 3:
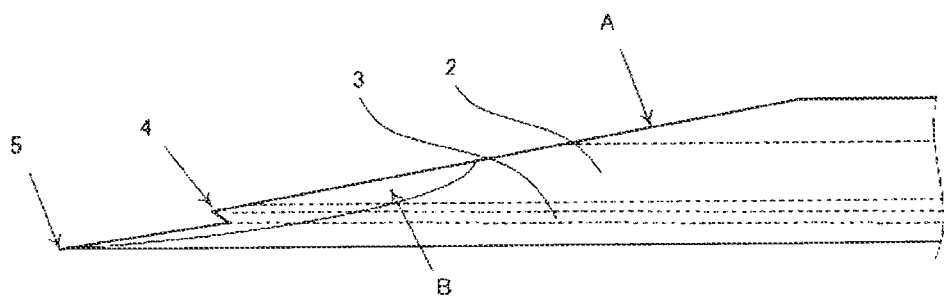
FIG. 3 is a side view of the needle for a living body according to the present invention in Example 1.

In the embodiment shown in FIGS. 1 to 3, the sampling hole 2 penetrates through the center of the needle. However, the sampling hole does not necessarily need to penetrate through the center of the needle and may be provided at any position. As described later, the needle of the present invention is provided with a cutting part 4 positioned between openings of the sampling and cooling holes 2, 3 on the pricking-end surface. Accordingly, it is necessary that the pricking tip 5, the opening of the cooling hole 3 and the opening of the sampling hole 2 be positioned in this order on the pricking-end surface.

The main body of the needle shown in FIG. 1 has a circular cross-section, but there is no restriction on the shape of the cross-section. It may be, for example, an elliptical, triangular, rectangular or hexagonal shape. In view of reducing the damage of the tissue sample, the main body preferably has a circular cross-section.

In the needle of FIG. 1, the pricking tip 5 is a vertex at which three planes meet. This means that the pricking tip 5 is in the shape formed by obliquely cutting a hollow ceramic capillary to form a flat bevel A and then by chamfering the bevel A to form flat bevels B and C not parallel to each other. Accordingly, the pricking tip 5 has a shape sharper than a simple bevel tip. Further, because of the bevels B and C, the opening of the cooling hole 3 is not formed in a plane, so as to form a cutting part 4 on the opening of the cooling hole 3 having a rectangular cross-sectional outline as shown in FIG. 2. The cutting part 4 appears to be a spike in the side view shown in FIG. 3. If the sectional shape of the cooling hole 3 has a straight outline in the portion adjacent to the sampling hole, the cutting part has a shape projecting toward the pricking tip. This means that, even if the cooling hole has a cross-section in a relatively simple shape, a cutting part having excellent ability in cutting off a tissue sample is easily formed by chamfering the end bevel. If the hole has a conventional circular cross-section, it is impossible to form a cutting part as excellent as that in cutting ability.

Thus, the cooling hole 3 does not have a circular cross-section. The cross-sectional shape is, for example, a rectangle shown in FIG. 1. Further, as described later, it may be a triangle, a trapezoid, or a semicircle having a straight outline in the portion adjacent to the sampling hole 2. Further, in order to form a sharper cutting part, the sectional shape of the cooling hole 3 may have an inside-curved outline in the portion adjacent the sampling hole 2. The cross-sectional shape of the cooling hole is described later in detail.

On the other hand, there is no particular restriction on the cross-sectional shape of the sampling hole. However, the sampling hole generally has a circular cross-sectional shape unless there is a particular reason. This is because it can be easily produced.

Example 2

Figure 4:
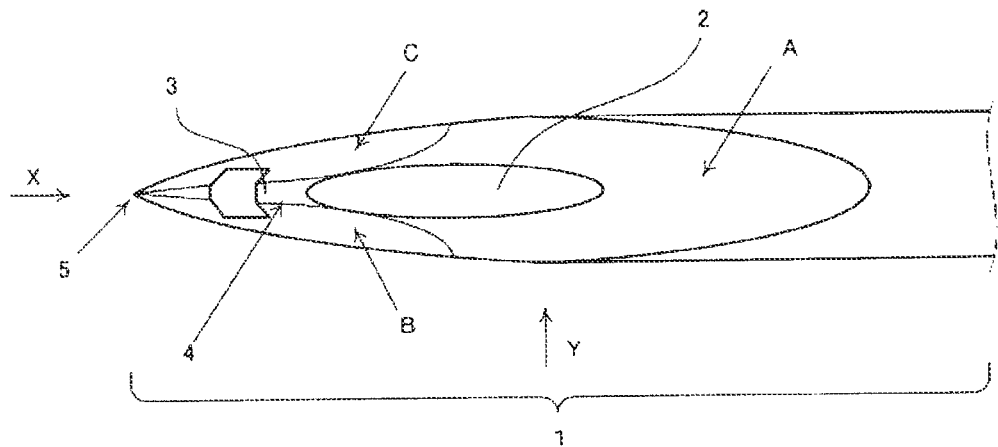
FIG. 4 is a plane view of the needle for a living body according to the present invention in Example 2.
Figure 5:
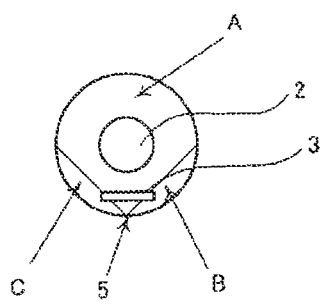
FIG. 5 is a front view of the needle for a living body according to the present invention in Example 2.
Figure 6:
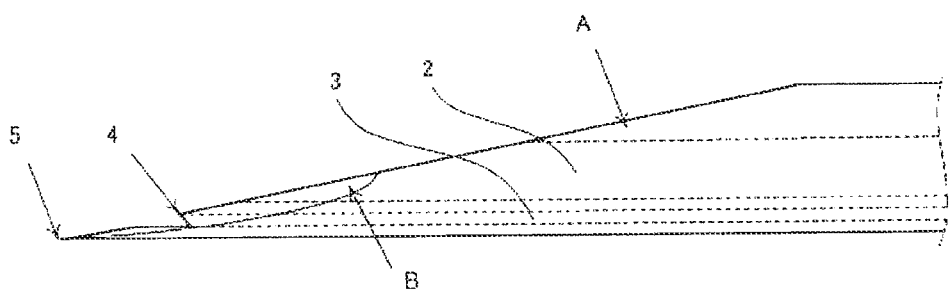
FIG. 6 is a side view of the needle for a living body according to the present invention in Example 2.

FIGS. 4 to 6 are a plane view, a front view and a side view, respectively, showing a pricking end of a needle 1 according to another embodiment of the present invention. The needle of this embodiment differs from that of Example 1 in the position of the cooling hole 3 and in the way of chamfering the end bevel. Nevertheless, it can be used in the same way as the needle of Example 1.

Example 3

FIG. 7 is a plane view showing a pricking end of a needle 1 according to still another embodiment of the present invention, and FIG. 8 is a front view thereof seen parallel to the longitudinal direction (in the direction indicated by the arrow X in FIG. 7). The needle of this embodiment is further provided with still another hole 6 penetrating through in the longitudinal direction. The penetrating hole 6 can be used, for example, for introducing a medicine for treating the pricked point. When the needle is pricked into a living body for harvesting a tissue sample, it is inevitable to injure the body. However, the injury can be reduced to a minimal degree by supplying an injection or an antiseptic solution when the tissue sample is harvested. Generally, after a tissue is sampled from a particular point of the body, it is very difficult to prick again "an injection needle" for supplying a medicine into that point. Accordingly, it is very preferable to harvest a tissue sample and to supply a medicine at the same time. This medicine is not restricted to a solution for treating the injury given by the needle, and hence it may be, for example, a remedy for malignant tumor cells. Accordingly, the present invention enables to harvest a tissue sample immediately before or after the remedy is injected.

Further, the penetrating hole 6 can be used not only for injecting a medicine but also for observing cells or tissues remaining after the sample is cut away. For example, a fiber scope is inserted into the hole 6. If the penetrating hole 6 serves as an observation hole, it becomes possible to observe a diseased part of a body, to harvest a sample of the cells, and to test or treat the diseased part at the same time. Consequently, it enables to certainly obtain more precise information.

The above penetrating hole 6 may be formed at any place. FIG. 9 shows examples of cross-sectional views in which holes 6 are placed at different positions. As shown in FIG. 9, the hole 6 may be positioned next to the sampling hole 2 on the side far from the cooling hole 3 (FIG. 9A, which corresponds to FIGS. 7 and 8), may be positioned nearer to the pricking tip than the cooling hole 3 (FIG. 9B), or may be positioned side by side with the sampling hole 2 (FIG. 9C). The needle may be provided with two or more penetrating holes 6.

Example 4

FIG. 10 is a plane view showing a pricking end of a needle 1 according to yet another embodiment of the present invention, and FIG. 11 is a view of the cross-section thereof perpendicular to the longitudinal direction. As shown in FIG. 11, the cooling hole 3 in this embodiment has a semicircular sectional outline but the cutting part 4 is formed by chamfering the bevel A. Since the sectional outline of the cooling hole 3 has a straight portion adjacent to the sampling hole 2, the formed cutting part 4 has a linear edge. Even if the sectional outline is neither a rectangle nor a semicircle, the cutting part 4 having the above shape can be formed provided that the outline has a straight portion adjacent to the sampling hole. This means that the sectional outline of the cooling hole 3 may be an inverted trapezoid shown in FIG. 12A or a triangle shown in FIG. 12B. If having a long sectional outline portion adjacent to the sampling hole, the cooling hole 3 can supply cooling gas widely and hence it can be expected to improve the efficiency of cooling the sample.

As described above, in order to form a cutting part 4 having a linear edge as shown in FIG. 10, it is necessary that the needle 1 have a bevel A at the pricking end and that, on the bevel A, the opening of the cooling hole 3 be positioned nearer to the pricking tip 5 than the opening of the sampling hole 2. Further, the cooling hole 3 preferably has such a cross-section perpendicular to the longitudinal direction that its sectional outline shape has a straight portion adjacent to the sampling hole.

Example 5

FIG. 13 is a plane view showing a pricking end of a needle 1 according to still yet another embodiment of the present invention, and FIG. 14 is a view of the cross-section thereof perpendicular to the longitudinal direction. The needle shown in FIGS. 13 and 14 has a pricking-end surface consisting of only a single bevel A not chamfered. Although the needle of this embodiment thus differs from that of FIG. 1 or others, it has a cutting part 4 projecting toward the pricking tip. That is because the cooling hole 3 has a crescent sectional outline as shown in FIG. 14. If the cooling hole 3 has a V-shaped sectional outline as shown in FIG. 15, a cutting part is formed that is like a chisel projecting toward the pricking tip. In a side view of the needle having the above structure, the cutting part does not appear to be a spike although that of Example 1 does. Nevertheless, the cutting part 4 of this needle has a sharp projecting shape.

As described above, in order to form a cutting part 4 having a sharp projecting shape as shown in FIG. 13, it is necessary that the needle 1 have a bevel A at the pricking end and that, on the bevel A, the opening of the cooling hole 3 be positioned nearer to the pricking tip 5 than the opening of the sampling hole 2. Further, the cooling hole 3 preferably has such a cross-section perpendicular to the longitudinal direction that its sectional outline shape is inside-curved at least at a portion adjacent to the sampling hole. In other words, the cooling hole 3 preferably has a sectional outline whose inner circumference bulges out toward the outer circumference of the needle.

Even in a needle having the above structure, the bevel A may be chamfered to form bevels B and C as shown in FIG. 1 or the like. In that case, the formed cutting part has a much sharper shape.

The needle of the present invention for a living body can have various shapes as described above. There is no particular restriction on the size thereof, and hence it may be freely determined according to the object body, the size of the aimed tissue sample and the like. However, the needle may have an outer diameter of generally 0.5 to 16.0 mm, preferably 1.0 to 8.0 mm. The sampling hole may have an inner diameter of 0.1 to 8.0 mm, preferably 0.3 to 6.0 mm. If the needle is provided with an optional penetrating hole for a fiber scope inserted therethrough or for supplying an injection or an antiseptic solution, the inner diameter thereof may be 0.05 to 2.0 mm, preferably 0.09 to 0.9 mm. In the case where the needle or the hole has a cross-sectional shape other than a circle, the above range can be applied to the diameter of a circle having the same area as the cross-section thereof. In the present invention, the cooling hole generally does not have a circular cross-sectional shape. However, the cooling hole can have a cross-sectional area corresponding to a circle having a diameter of 0.1 to 8.0 mm, preferably 0.3 to 6.0 mm.

The width of the sampling hole is preferably almost the same as that of the cooling hole. Here, if the holes have circular cross-sections, the diameters thereof are regarded as the widths. If the holes have cross-sectional shapes other than circles, the width of each hole is determined by the length thereof perpendicular to the straight line connecting between the centers or centroids of the holes. For example, if the needle has a cross-section shown in FIG. 9A, the diameter of the circular sampling hole 2 preferably has almost the same length as the long side of the rectangular cooling hole 3. If the holes have almost the same widths, the tissue to be cut off is cooled necessarily and sufficiently while being kept from unnecessary load, so as to harvest the sample efficiently.

The needle of the present invention can have a pricking tip in any shape as long as it can be pricked into a living body. However, the sharper the pricking tip is, the less the tissue sample tends to be damaged. Accordingly, the pricking tip is preferably as sharp as possible. At the pricking end of the needle, the major bevel (bevel A) is preferably inclined at an angle of generally 3 to 45°, preferably 8 to 30°, to the longitudinal direction of the needle.

As shown in Examples, the cutting part 4 normally has a shape of a projecting edge. However, there is no particular restriction on the shape thereof as long as it can cut the tissue sample off. For example, the cutting part may be like a chisel projecting toward the pricking tip, as shown in Example 1.

Further, it may be like a saw or a straight knife. Since easily produced and having high cutting ability, the cutting part preferably has a shape of a chisel.

The needle according to the present invention is made of ceramics, as described above. Examples of the ceramics include metal oxides, silicides, fluorides and borides. Any of them can be used, but oxides are preferred and zirconium oxide is particularly preferred. Most preferred is partially stabilized zirconia, which is zirconium oxide doped with at least one of yttrium oxide, aluminum oxide, cerium oxide and hafnium oxide. Since improved in strength and in toughness, partially stabilized zirconia is particularly preferred. The needle of the present invention may be a metal- or other hard material-made needle coated with a film of the above ceramics. However, if the ceramic coating film peels off, the needle may cause injury current and/or fragments of the ceramic film may contaminate the sample or may fall into the living body. The needle, therefore, is preferably fully made of ceramics.

The whole or surface of the needle according to the present invention is made of ceramics, and is so stable that it can be repeatedly sterilized to use. This means that the needle of the present invention is hardly impaired even if sterilized with alcohol vapor at as high a temperature as 130° C. or more in high-pressure alcohol vapor sterilization or even if subjected to various other sterilizations such as normal sterilization by boiling and γ-ray sterilization. Further, after thermal treatment at such a higher temperature as is, for example, 600 to 700° C., it can be crashed to be scrapped. This means that secondary infection can be easily prevented, and hence the needle of the present invention after being used can be easily disposed of. The above temperature necessary for the thermal treatment is much lower than about 1000° C. or more, at which conventional metal needles must be treated before being scrapped, and hence the needle of the present invention is very advantageous also from the viewpoints of disposal treatment and of thermal energy cost.

There is no particular restriction on how the needle of the present invention is produced. For example, it can be produced by extrusion molding, injection molding or press molding. First, according to one of those molding processes, powdery ceramic material is molded into a capillary. The capillary is then sintered to form a needle body provided with penetrating holes, and the needle body is obliquely cut and chamfered, if necessary, to produce the needle according to the present invention.

The needle of the present invention for a living body is used, for example, in the following manner.

First, the pricking tip 5 is pressed onto a living body to stick the needle, and the opening of the sampling hole 2 is brought to the aimed position where a tissue is to be sampled. The sampling hole is beforehand connected to a pressure-reducing equipment such as a vacuum pump, and the cooling hole is beforehand connected to a cooling-gas supplying equipment such as a gas cylinder.

Subsequently, the inner pressure of the sampling hole 2 is reduced to aspirate the tissue, and at the same time, cooling gas is supplied from the cooling hole 3 so as to freeze or semi-freeze a portion of the tissue to be sampled. This freezing or semi-freezing is for the purpose of weakening binding of the tissue to be sampled. Accordingly, the cooling gas must have a temperature enough to freeze or semi-freeze the tissue. The tissue does not need to be frozen completely. It is enough to weaken the bonding to such a degree that the tissue can be easily cut off with the cutting part, and hence the complete freezing is not necessarily needed and even the semi-freezing can attain the purpose. Since frozen or semi-frozen to be made partly fragile, the tissue kept aspirated through the sampling hole 2 is easily cut off from the living body with the cutting part 4 positioned between the openings of the sampling and cooling holes 2, 3. Thus, the tissue sample is harvested by aspiration.

As described above, since positioned between the openings of the sampling and cooling holes 2, 3, the cutting part 4 can certainly and easily cut off the tissue to be sampled.

It is also described above that the needle of the present invention may be provided with another penetrating hole for supplying a medicine. This hole can be used for the purpose of introducing a solution for treating injury caused either by sampling the tissue or before the needle is pricked. For example, first the needle of the present invention is pricked to harvest a tissue sample through the sampling hole, and then the harvested sample is examined to obtain information. After that, based on the obtained information, a proper medicine is introduced. In this way, it is possible to examine and treat the injured part at the same time.

The pricking tip can be brought to the sampling position in the living body by use of magnetic resonance imaging (hereinafter, referred to as MRI), computer tomography (hereinafter, referred to as CT) or ultrasonic imaging. In the case where the needle of the present invention is fully made of ceramics, it contains neither electroconductive nor magnetic substance. Accordingly, the pricking tip can be monitored by MRI or the like to be controlled. As for conventional needles comprising metal substances, that is impossible. Because of the excellent characteristics described above, the needle of the present invention enables to harvest and/or treat a tissue while monitoring the position of the pricking tip accurately.

Further, since having excellent strength and toughness in itself, the needle of the present invention can be used singly. However, the needle may be encased in a sleeve. In that case, first the sleeve is pricked into a living body without bringing the needle encased therein into contact with the body. Thereafter, the tip of the sleeve is brought to the sampling point, and then the needle is pushed out from the sleeve to harvest a sample.

Thus, the needle for a living body according to the present invention makes it possible to harvest a tissue sample certainly and stably while reducing damage of the sample to a minimal degree. Accordingly, it becomes possible to obtain precise information, based on which accurate diagnosis and proper treatment can be carried out. Consequently, the present invention can fully satisfy severe requirements in medical fields.

The invention claimed is:

1. A needle for a living body made of ceramics and used for harvesting a tissue sample from a living body, comprising:
   a pricking end surface terminating in a distal pricking tip;
   a sampling hole extending through the needle for sample aspiration;
   a cooling hole extending through the needle for supplying cooling gas; and
   a cutting part for cutting off said tissue sample; wherein said sampling hole and said cooling hole have openings on said pricking end surface and said cutting part is provided between said openings, wherein said cutting part projects from said pricking end surface toward said distal pricking tip.

2. The needle for a living body according to claim 1, wherein said ceramics is zirconium oxide.

3. The needle for a living body according to claim 1, wherein said pricking end surface is a bevel in which the opening of said cooling hole is positioned nearer to the distal pricking tip than the opening of said sampling hole, and said cooling hole has a cross-sectional outline shape in a direction perpendicular to a longitudinal direction that is straight or inside-curved at least in a portion adjacent to the sampling hole.

4. The needle for a living body according to claim 1, which is further provided with still another hole penetrating through for supplying a medicine.

5. A tissue-sampling device comprising:
the needle for a living body according to claim 1, a pressure-reducing equipment connected to said sampling hole extending through the needle for sample aspiration, and a cooling-gas supplying equipment connected to said cooling hole extending through the needle for supplying cooling gas.

6. The tissue-sampling device according to claim 5, wherein said needle for a living body is encased in a sleeve.

7. A process for sampling a tissue using the needle for a living body according to claim 1, the process comprising the steps of:
pricking the needle into a living body;
aspirating tissue through said sampling hole while supplying cooling gas through said cooling hole so as to make a portion of the tissue fragile by freezing or semi-freezing; and
cutting off the frozen or semi-frozen portion of the tissue with said cutting part to harvest the tissue by aspiration.

* * * * *